(12) United States Patent
Rendahl et al.

(10) Patent No.: US 6,745,613 B2
(45) Date of Patent: Jun. 8, 2004

(54) METHOD AND SYSTEM FOR DETERMINING THE TYPE OF FUEL USED TO POWER A VEHICLE

(75) Inventors: Craig S. Rendahl, Tucson, AZ (US); Theresa A. Foley, Delavan, WI (US)

(73) Assignee: SPX Corporation, Charlotte, NC (US)

( * ) Notice: Subject to any disclaimer, the term of this patent is extended or adjusted under 35 U.S.C. 154(b) by 0 days.

(21) Appl. No.: 09/928,720

(22) Filed: Aug. 13, 2001

(65) Prior Publication Data

US 2003/0037594 A1 Feb. 27, 2003

(51) Int. Cl.$^7$ .............................................. G01M 15/00
(52) U.S. Cl. ...................................................... 73/35.02
(58) Field of Search ........................... 73/23.31, 28.01, 73/28.04, 31.03, 61.75, 786, 861.04, 861.21, 35.02; 123/436, 443, 488, 492, 527, 435, 491

(56) References Cited

U.S. PATENT DOCUMENTS

| | | | |
|---|---|---|---|
| 3,696,247 A | 10/1972 | McIntosh et al. ....... 250/83.3 H |
| 3,811,776 A | 5/1974 | Blau, Jr. ....................... 356/51 |
| 3,957,372 A | 5/1976 | Jowett et al. ................. 356/51 |
| 3,958,122 A | 5/1976 | Jowett et al. ............... 250/346 |
| 3,973,848 A | 8/1976 | Jowett et al. ................. 356/51 |
| 4,012,144 A | 3/1977 | Hedelman ..................... 356/73 |
| 4,013,260 A | 3/1977 | McClatchie et al. ........ 250/343 |
| 4,160,373 A | 7/1979 | Fastaia et al. .................. 73/23 |
| 4,171,909 A | 10/1979 | Kramer et al. ................ 356/73 |
| 4,204,768 A | 5/1980 | N'Guyen ..................... 356/243 |
| 4,310,249 A | 1/1982 | Kramer ....................... 356/414 |
| 4,348,732 A | 9/1982 | Kreft ........................... 364/571 |
| 4,372,155 A | 2/1983 | Butler et al. ................... 73/114 |
| 4,390,785 A | 6/1983 | Faulhaber et al. ........... 250/330 |
| 4,432,316 A | 2/1984 | Ogita ........................... 123/328 |
| 4,490,845 A | 12/1984 | Steinbruegge et al. ......... 382/1 |
| 4,560,873 A | 12/1985 | McGowan et al. .......... 250/339 |
| 4,602,160 A | 7/1986 | Mactaggart .................. 250/341 |
| 4,632,563 A | 12/1986 | Lord, III ..................... 356/437 |
| 4,638,345 A | 1/1987 | Elabd et al. ................... 357/24 |
| 4,663,522 A | 5/1987 | Welbourn et al. ........ 250/223 R |
| 4,678,914 A | 7/1987 | Melrose et al. .............. 250/343 |
| 4,687,934 A | 8/1987 | Passaro et al. ............... 250/343 |
| 4,710,630 A | 12/1987 | Kuppenheimer, Jr. et al. ............................ 250/353 |
| 4,746,218 A | 5/1988 | Lord, III ..................... 356/437 |
| 4,795,253 A | 1/1989 | Sandridge et al. ............. 356/51 |
| 4,818,705 A | 4/1989 | Schneider et al. ........... 436/164 |
| 4,829,183 A | 5/1989 | McClatchie et al. ......... 250/346 |
| 4,868,622 A | 9/1989 | Shigenaka .................... 357/30 |
| 4,875,084 A | 10/1989 | Tohyama ...................... 357/30 |
| 4,914,719 A | 4/1990 | Conlon et al. ............... 250/339 |

(List continued on next page.)

OTHER PUBLICATIONS

Bureau of Automotive Repair; "On Road Emissions Measurement System (OREMS) Specifications"; OREMS Specifications–Version O, Jan. 28, 2002; 2002 California DCA/BAR.

(List continued on next page.)

Primary Examiner—Kamand Cuneo
Assistant Examiner—Monica D. Harrison
(74) Attorney, Agent, or Firm—Baker & Hostetler LLP

(57) ABSTRACT

A method for determining the type of fuel used by a vehicle includes receiving hydrocarbon speciation and nitrogen-oxygen compound data from an emissions sensor. The hydrocarbon speciation data is compared to one or more hydrocarbon threshold levels, and each threshold level corresponds to an anticipated fuel type. The nitrogen-oxygen compound data is compared to one or more nitrogen-oxygen compound threshold levels, and each threshold level corresponds to an anticipated fuel type. Based on the comparison of the hydrocarbon speciation and nitrogen-oxygen compound data to threshold levels, an anticipated fuel type is determined.

21 Claims, 7 Drawing Sheets

U.S. PATENT DOCUMENTS

| | | | |
|---|---|---|---|
| 4,924,095 A | 5/1990 | Swanson, Jr. | 250/338.5 |
| 4,963,023 A | 10/1990 | Goldovsky et al. | 356/308 |
| 4,999,498 A | 3/1991 | Hunt et al. | 250/338.5 |
| 5,002,391 A | 3/1991 | Wolfrum et al. | 356/307 |
| 5,041,723 A | 8/1991 | Ishida et al. | 250/339 |
| 5,061,854 A | 10/1991 | Kroutil et al. | 250/339 |
| 5,076,699 A | 12/1991 | Ryan et al. | 356/437 |
| 5,157,288 A | 10/1992 | Hill | 307/511 |
| 5,185,648 A | 2/1993 | Baker et al. | 257/189 |
| 5,210,702 A | 5/1993 | Bishop et al. | 364/496 |
| 5,239,860 A | 8/1993 | Harris et al. | 73/61.48 |
| 5,252,828 A | 10/1993 | Kert et al. | 250/339 |
| 5,255,511 A | 10/1993 | Maus et al. | 60/274 |
| 5,307,626 A | 5/1994 | Maus et al. | 60/274 |
| 5,319,199 A | 6/1994 | Stedman et al. | 250/338.5 |
| 5,332,901 A | 7/1994 | Eckles et al. | 250/345 |
| 5,343,043 A | 8/1994 | Johnson | 250/338.5 |
| 5,361,171 A | 11/1994 | Bleier | 359/855 |
| 5,371,367 A | 12/1994 | DiDomenico et al. | 250/338.5 |
| 5,373,160 A | 12/1994 | Taylor | 250/338.5 |
| 5,401,967 A | 3/1995 | Stedman et al. | 250/338.5 |
| 5,418,366 A | 5/1995 | Rubin et al. | 250/338.5 |
| 5,489,777 A | 2/1996 | Stedman et al. | 250/338.5 |
| 5,498,872 A | 3/1996 | Stedman et al. | 250/338.5 |
| 5,545,897 A | 8/1996 | Jack | 250/339.13 |
| 5,583,765 A | 12/1996 | Kleehammer | 364/423.098 |
| 5,591,975 A | 1/1997 | Jack et al. | 250/338.5 |
| 5,621,166 A | 4/1997 | Butler | 73/116 |
| 5,644,133 A | 7/1997 | Didomenico et al. | 250/338.5 |
| 5,666,923 A * | 9/1997 | Collier, Jr. et al. | 123/488 |
| 5,719,396 A | 2/1998 | Jack et al. | 250/338.5 |
| 5,726,450 A | 3/1998 | Peterson et al. | 250/338.5 |
| 5,797,682 A | 8/1998 | Kert et al. | 374/123 |
| 5,812,249 A | 9/1998 | Johnson et al. | 356/28 |
| 5,831,267 A | 11/1998 | Jack et al. | 250/338.5 |
| 5,922,948 A | 7/1999 | Lesko et al. | 73/117.3 |
| 6,009,742 A * | 1/2000 | Balko | 73/23.31 |
| 6,057,923 A | 5/2000 | Sachse | 356/364 |
| 6,230,087 B1 | 5/2001 | Didomenico et al. | 701/29 |
| 6,307,201 B1 | 10/2001 | Didomenico et al. | 250/339.13 |

OTHER PUBLICATIONS

Jiménez–Palacios, José Luis; "Understanding and Quantifying Motor Vehicle Emissions with Vehicle Specific Power and TILDAS Remote Sensing"; Massachusetts Institute of Technology, Feb. 1999.

Radian Corp.; "Developing an Inspection/Maintenance Program for Alternatively–Fueled Vehicles"; 1993.

Islam, Muhammed, Rendahl, Craig S., Cors, Rebecca; "Wisconsin's Remove Vehicle Emissions Sensing Study"; Final Report 1995.

Walsh, P.A., Gertler, A.W.; "Texas 1996 Remote Sensing Feasibility Study"; Final Report 1997.

Popp, Peter J.; "Development of a High–Speed Ultraviolet Spectrophotometer Capable of Real–Time NO and Aromatic Hydrocarbon Detection in Vehicle Exhaust"; pp. 4–3 & 4–12;Coordinating Research Council 1997.

McVey, Iain Frederick; "Development of a Remote Sensor for Mobile Source Nitric Oxide"; University of Denver 1992.

Beaton, S.P., Bishop, G.A. and Stedman D.H.; Emissions Characteristics of Mexico City Vehicles; pp. 42, 1424–1429; Journal of Air and Waste Management Assoc. 1992.

Zhang, Yi, Stedman, Donald H., Bishop, Gary A., Beaton, Stuart P., Guenther, Paul L. and McVey, Iain F.; "Enhancement of Remote Sensing for Mobile Source Nitric Oxide"; Journal of Air & Waste Management 1996; vol. 46, pp. 25–29.

Popp, Peter John; "Remote Sensing of Nitric Oxide Emissions from Planes, Trains and Automobiles"; University of Denver 1999.

Zhang, Yi, Stedman, Donald H., Bishop, Gary A., Beaton, Stuart P., and Guenther, Paul L.; "Worldwide On–Road Vehicle Exhaust Emissions Study by Remote Sensing"; Environmental Science & Technology 1995;Vol 29#9. pp. 2286–2294.

Glover, Edward L., Mickelsen, Jan and McClement Dennis; Evaluation of Methods to Determine Catalyst Efficiency in the Inspection/Maintenance Process; Society of Automotive Engineers; SAE#9600092.

Butler, James, Gierczak, Christine and Liscombe Paula; "Factors Affecting the NDIR Measurement of Exhaust Hydrocarbons"; Coordinating Research Council 1995; pp. 4–171 & 4–190.

MacKay, Gervase I., Nadler, S. Don, Karecki, David R., Schiff, Harold I., Butler, James W., Gierczak, Christine A. and Jesion, Gerald; "Final Phase 1b Report to the CRC and NREL for Research Performed Under Agreement No. VE–8–2"; Coordinating Research Council 1994.

Peterson, James E. and Stedman, Donald H.; "Find and Fix the Polluters"; Chemtech 1992, pp. 47–53.

Bishop, Gary A. and Stedman Donald H.; "Infrared Emissions and Remote Sensing"; Journal of Air and Waste Management Assoc. 1992; vol. 42#5, pp. 695–697.

Bishop, Gary A., Starkey, John R., Ihlenfeldt, Anne, Williams, Walter J. and Stedman Donald H.; "IR Long–Path Photometry: A Remote Sensing Tool for Automobile Emissions"; Analytical Chemistry 1989; vol. 61#10, pp. 671A–677A.

Axelsson, Hakan, Eilard, Anders, Emanuelsson, Annika, Galle, Bo, Edner, Hans, Regnarson Par and Kloo Henrik; "Measurement of Aromatic Hydrocarbons with the DOAS Technique"; Applied Spectroscopy 1995; vol. 49#9, pp. 1254–1260.

Baum, Marc M., Kiyomiya, Eileen S., Kumar Sasi and Lappas, Anastasios M. ' "Multicomponent Remote Sensing of Vehicle Exhaust by Dispersive Absorption Spectroscopy. 1. Effect of Fuel Type and Catalyst Performance"; Environmental Science and Technology 2000; pp. 34 & 2851–2858.

Stedman, Donald H. and Smith, Dennis L.; "$NO_x$ Data by Remote Sensing"; Coordinating Research Council 1995; pp. 4–47 & 4–63.

Shore, P.R. and Devries, R.S.; "On–line Hydrocarbon Speciation Using FTIR and CI–MS"; Society of Automotive Engineers 1992; SAE #922246.

Bishop, Gary A. and Stedman, Donald H.; "On–Road Carbon Monoxide Emission Measurement Comparisons for the 1988–1989 Colorado Oxy–Fuels Program"; Environmental Science & Technology 1990; pp. 24 & 843–847.

Stedman, Donald H., Bishop, Gary, Peterson, James E., and Geunther, Paul L.; "On–Road CO Remote Sensing in the Los Angeles Basin"; CA–EPA (CARB) 1991; pp. 24 & 843–847.

x–Rite Incorporated; "A Guide to Integrating Sphere Theory and Applications"; 2002; www.labsphere.com.

Geunther, Paul L., Stedman, Donald H., Bishop, Gary A., Beaton, Stuaret P., Bean, James H. and Quine Richard W.; "A Hydrocarbon Detector for the Remote Sensing of Vehicle Exhaust Emissions"; Review of Scientific Instruments 1994; vol. 66(4), pp. 3024–3029.

Stephens, Robert D., Mulawa, Patricia A., Giles, Michael T., Kennedy, Kenneth G., Groblicki, Peter J. and Cadle, Steven H.; "An Experimental Evaluation of Remote Sensing–Based Hydrocarbon Measurements: A Comparison to FID Measurements"; Journal of Air and Waste Management Assoc. 1996; pp. 46 & 148–158.

Stedman, Donald H.; "Automobile Carbon Monoxide Emissions"; Environmental Science and Technology 1989; vol. 23#2, pp. 147–149.

Adachi, Masayuki, Yamagishi, Yutaka, Inoue Kaori and Ishida, Kozo; "Automotive Emissions Analyses using FTIR Spectrophotometer"; Society of Automotive Engineers 1992; SAE #920723.

Koplow, Michael D., Jimenez, Jose L., Nelson, David D., Schmidt, Stephan E.; "Characterization of On–Road Vehicle NO Emissions by Means of a TILDAS Remote Sensing Instrument"; Coordinating Research Council 1997; pp. 8–35 & 8–62.

Guenther, Paul Leonard; "Contributions to On–Road Remoter Sensing of Automobile Exhaust"; University of Denver 1992.

Cox, Frank W., Walls, John R. and Carrel, Mark W.; "Determination of Catalyst Oxidation and Reduction Efficiencies from Tailpipe Emissions Measurements"; Society of Automotive Engineers 1997; SAE #972911.

Lawson, Douglas R., Groblicki, Peter J., Stedman, Donald H., Bishop, Gary A. and Guenther Paul L.; "Emissions from In–Use Motor Vehicles in Los Angeles: A Pilot Study of Remote Sensing and the Inspection and Maintenance Program"; Journal of Air and Waste Management Assoc. 1990; vol. 40#8, pp. 1096–1105.

Stedman, Donald H., Bishop, Gary A. and Pitchford, Marc L.; "Evaluation of a Remote Sensor for Mobile Source CO EMISSIONS"; University of Denver 1991; Rpt.# EPA 600/4–90/032.

McLaren, Scott E., Stedman, Donald H., Greenlaw, Pamela D., Bath, Raymond J., and Spear, Richard D.; Comparison of an Open Path UV and FTIR Spectrometer; Air and Waste Management Assoc. 1992; vol. 92–73.10.

Bishop, Gary A., Zhang, Yi, McLaren, Scott E., Guenther, Paul L., Beaton, James E., Stedman, Donald H., Duncan, John W., McArver, Alexander Q., Pierson, William R., Groblicki, Peter J., Knapp, Kenneth T., Zweidinger, Roy B. and Day, Frank J.; Enhancements of Remote Sensing for Vehicle Emissions in Tunnels; Journal of Air and Waste Management 1994; vol. 44, pp. 169–175.

McLaren, Scott E. and Stedman Donald H.; "Flux Measurements Using Simultaneous Long Path Ultraviolet and Infrared Spectroscopy"; Air and Waste Management Assoc. 1990; vol. 90–86.6.

Bishop, Gary A., McLaren, Scott E., Stedman, Donald H., Pierson, William R., Zweidinger, Roy B. and Ray, William D; "Method Comparisons of Vehicle Emissions Measurements in the Fort McHenry and Tuscarora Mountain Tunnels"; Atmospheric Environment 1996; vol. 30#12, pp. 2307–2316.

McLaren, Scott; "Open Path Spectrometers for Atmospheric Monitoring"; University of Denver 1995.

Stedman, Donald H. and Bishop, Gary A.; "An Analysis of On–Road Remote Sensing as a Tool for Automobile Emissions Control"; Illinois Dept. of Energy & Natural Resources 1990; ILENR/RE–AQ–90/05.

Stedman, Donald H., Peterson, James E. and McVey, Iain F.; "On–Road Carbon Monoxide and Hydrocarbon Remote Sensing in the Chicago Area"; Illinois Dept. of Energy & Natural Resources 1991; ILENR/RE–AQ–91/14.

Lyons, Carol E. and Stedman, Donald H.; "Remote Sensing Enhanced Motor Vehicle Emissions Control for Pollution Reduction in the Chicago Metropolitan Area: Siting and Issue Analysis"; Illinois Dept. of Energy & Natural Resources 1991; ILENR/RE–AQ–91/15.

Durbin, Thomas D., Truex, Timothy J. and Norbeck, Joseph M.; "Particulate Measurements and Emissions Characterizations of Alternative Fuel Vehicle Exhaust"; National Renewable Energy Laboratory 1998; NREL/SR–540–25741; Subcont# ACI–71–6637–01.

DiDomenico, John, Johnson, Jim, Webster, Jason and Rendahl, Craig S.; "Preliminary Results from Cold Start Sensor Testing"; Coordinating Research Council 1997; pp. 4–71 & 4–72.

Stephens, Robert D. and Cadle, Steven H.; "Remote Sensing Measurements of Carbon Monoxide Emissions from On–Road Vehicles"; Journal of Air and Waste Management Assoc. 1991; vol. 41#1, pp. 39–46.

Jimenez, Jose L., McRae, Gregory J., Nelson, David D., Zahniser, Mark S. and Kolb, Charles E.; "Remote Sensing of NO and $NO_2$ Emissions from Heavy–Duty Diesel Trucks Using Tunable Diode Lasers"; Environmental Science & Technology 2000; pp. 34 & 2380–2387.

Stedman, Donald H., Bishop, Gary A., Guenther, Paul L., Peterson, James E., Beaton, Stuart P. and McVey, Iain F.; "Remote Sensing of On–Road Vehicle Emissions"; University of Denver 1992; Contract #VE–8–1.

Singer, Brett C., Harley, Robert A., Littlejohn, David, Ho, Jerry and Vo, Thu; "Scaling of Infrared Remote Sensor Hydrocarbon Measurements for Motor Vehicle Emission Inventory Calculations"; Environmental Science and Technology 1998; vol. 32#21, pp. 3241–3428.

Atkinson, Chris M., McKain, David L., Gautam, Mridul, El–Gazzar, Laila, Lyons, Donald W. and Clark, Nigel N.; "Speciation of Heavy Duty Diesel Engine Exhaust Emissions"; Coordinating Research Council 1995; pp. 5–71 & 5–92.

Chaney, Lucian W.; "The Remote Measurement of Traffic Generated Carbon Monoxide"; Journal of Air Pollution Control Assoc. 1983; vol. 33#3, pp. 220–222.

Todd, Michael and Barth, Michael; "The Variation of Remote Sensing Emission Measurements with Respect to Vehicle Speed and Acceleration"; Coordinating Research Council 1995; pp. 4–1 & 4–14.

Hoshizaki, H., Wood, A.D and Kemp, D.D.; "Vehicle Inspection Instrumentation"; Lockheed Missiles & Space Company 1973; ARB–3C–235–7.

Sigsby, Jr., John E., Tejada, Silvestre and Ray, William; "Volatile Organic Compound Emissions from 46 In–Use Passenger Cars"; Environmental Science & Technology 1987; pp. 21 & 466–475.

* cited by examiner

METHOD AND SYSTEM FOR DETERMINING THE TYPE OF FUEL USED TO POWER A VEHICLE

FIELD OF THE INVENTION

The present invention relates generally to vehicle emissions sensing systems. More particularly, the present invention relates to a method and system for determining, based on emissions data, the type of fuel that is used to power a vehicle.

BACKGROUND OF THE INVENTION

To determine whether a vehicle is compliant with emissions standards, a knowledge of the fuel type is required, as different fuel types will exhibit different mixes of hydrocarbon species in exhaust. For example, a mix of hydrocarbons emissions that may comply with applicable emissions standards for diesel fuel may not comply with emissions standards that are applicable to another fuel such as gasoline. Thus, if the type of fuel that is used by the vehicle is not known, false readings of compliance or noncompliance with emission standards may result. In addition, as alternative fuels are developed, additional methods of determining fuel type become important to determine compliance with fuel type restrictions, manufacturer's specifications, and emission regulations.

Unfortunately, current vehicle emissions measurement systems are not capable of automatically and reliably determining the type of fuel that is used to power the engine of a vehicle. This problem exists in both closed path and open path emissions measurement systems. In a closed path system, in which the emissions sensor is directly connected to the exhaust of the vehicle, attempts to overcome this problem have been limited to asking the vehicle's owner what type of fuel has been placed into the vehicle's fuel tank, as well as directly siphoning fuel and performing tests on such fuel. However, asking the vehicle's owner is often an unreliable method of determining fuel type, and chemical analysis of fuel contained in the fuel tank is expensive and time-consuming. For open path vehicular emissions measurement systems, in which emissions data are collected by a means other than a direct connection to the tailpipe, such as a remote sensor that analyzes the components of emissions, the problem exists to a greater degree, as open path vehicular emissions systems are desirable in areas along roadways where, because the vehicle is moving, the vehicle's owner cannot be asked fuel type, and fuel samples cannot be taken.

Also with an open path vehicular emissions testing system, the fuel type of a tested vehicle is obtained by matching the vehicle's license plate against registration records that include fuel type information. This information can be incorrect because of benign misinformation in the registration database, or intentional, if a vehicle owner converts the vehicle to a different fuel type without informing the keepers of the registration database. For example, a vehicle registered to be diesel-powered is most likely to be exempted from periodic emissions inspections. However if the vehicle is converted to being gasoline powered without the knowledge of the keepers of the registration database, the vehicle should become subject to periodic inspection. This is a circumvention of vehicular emissions laws.

Accordingly, it is desirable to provide an improved method and system for automatically determining the type of fuel used to power a vehicle based on data corresponding to the emissions of the vehicle. It is also desirable that the method and system be capable of application in both closed path and open path vehicle emissions measurement systems.

SUMMARY OF THE INVENTION

It is therefore a feature and advantage of the present invention to provide a method of automatically determining the type of fuel used to power a vehicle based on emissions data.

The above and other features and advantages are achieved through the use of a novel fuel type determination method and system as herein disclosed. In accordance with one embodiment of the present invention, a method of determining the type of fuel used by a vehicle includes the steps of receiving first data and second collected by an emissions sensor. The first data corresponds to at least two measured hydrocarbon concentrations in a vehicle exhaust stream; while the second data corresponds to measured nitrogen-oxygen compound concentrations in the vehicle exhaust stream. The method also includes the steps of identifying at least one hydrocarbon threshold level corresponding to a first fuel type, comparing the first data to at least one of the hydrocarbon threshold levels; and determining whether the measured hydrocarbon concentrations correspond to at least one of the hydrocarbon threshold levels. In addition, the method includes identifying at least one nitrogen-oxygen compound threshold level corresponding to the first fuel type, comparing the second data to at least one of the nitrogen-oxygen compound threshold levels, and determining whether the measured nitrogen-oxygen compound concentrations correspond to at least one of the nitrogen-oxygen compound threshold levels.

In accordance with this embodiment, if the first determining step determines that the measured hydrocarbon concentrations do not correspond to at least one of the hydrocarbon threshold levels, the method may comprise the additional steps of identifying at least one hydrocarbon threshold level corresponding to a second fuel type, comparing the data to at least one of the hydrocarbon threshold levels corresponding to the second fuel type, and determining whether the measured hydrocarbon concentrations correspond to at least one of the hydrocarbon threshold levels corresponding to the second fuel type. In addition, if the second determining step determines that the measured nitrogen-oxygen compound concentrations do not correspond to at least one of the nitrogen-oxygen compound threshold levels, the method may include the additional steps of: identifying at least one nitrogen-oxygen compound threshold level corresponding to a second fuel type, comparing the second data to at least one of the nitrogen-oxygen compound threshold levels corresponding to the second fuel type, and determining whether the measured nitrogen-oxygen compound concentrations correspond to at least one of the nitrogen-oxygen compound threshold levels corresponding to the second fuel type.

The threshold levels are preferably stored in a computer memory or carrier, and may optionally comprise a percentage or a range. When the threshold level comprises a percentage, correspondence preferably comprises a determination that the measured concentration is equal to or greater than the percentage. Where the threshold level comprises a range, correspondence preferably comprises a determination that the measured concentration falls within the range.

In accordance with an alternate embodiment of the present invention, a method of determining the type of fuel used by a vehicle includes the step of receiving data collected by an emissions sensor, wherein the data corresponds to a plurality of measured hydrocarbon and nitrogen-oxygen compound concentrations in a vehicle exhaust stream. The method also includes calculating, for each of a plurality of possible fuel types, an associated probability. The associated probability corresponds to the plurality of measured hydrocarbon and nitrogen-oxygen compound concentrations. The method also includes selecting a highest probability from the associated probabilities and reporting the possible fuel type having the associated probability that is the highest probability.

In accordance with either of the above-described embodiments, the fuel types preferably include diesel fuel, gasoline, compressed natural gas, methanol, reformulated gasoline, and/or liquified petroleum gas. Where a fuel type comprises diesel fuel, the methods preferably include comparing measured concentrations to threshold levels of methane and carbonyl species comparing measured concentrations to threshold concentrations of nitrogen dioxide. Where a fuel type comprises compressed natural gas, and the methods preferably include summing measured concentrations of alkanes, alkenes, alkynes, and methane and comparing the measured concentration of methane to the total sum. Where a fuel type comprises liquified petroleum gas, the method preferably includes (i) determining a total hydrocarbon measurement comprising a sum of measured concentrations of alkanes, alkenes, alkynes, and methane; (ii) determining a percentage of propane relative to the total hydrocarbon measurement; and (iii) determining whether the percentage of propane exceeds a predetermined propane threshold. Where a fuel type comprises methanol or reformulated gas, the method preferably includes: (i) identifying relative concentrations of carbon, hydrogen, and oxygen that are typical for a reference fuel; (ii) determining whether the relative concentration of oxygen is greater than zero; (iii) selecting, from the measured hydrocarbon concentrations, a first concentration corresponding to alkanes and a second concentration corresponding to methanol and reformulated gasoline species; (iv) scaling the first concentration and the second concentration to adjust for at least one interference; and (iv) comparing the first concentration and the second concentration.

Another embodiment of the present invention provides a system for the implementation of one or more of the above-described methods. The system includes an emissions sensor or other means capable of measuring hydrocarbon and nitrogen-oxygen compound concentrations in a vehicle exhaust stream. The system also includes a processor in communication with the emissions sensor, and a memory or other carrier in communication with the processor. The carrier contains computer program instructions that instruct the processor to implement one or more of the above-described methods.

There have thus been outlined the more important features of the invention in order that the detailed description thereof that follows may be better understood, and in order that the present contribution to the art may be better appreciated. There are, of course, additional features of the invention that will be described below and which will form at least part of the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract included below, are for the purpose of description and should not be regarded as limiting in any way.

As such, those skilled in the art will appreciate that the concept and objectives, upon which this disclosure is based, may be readily utilized as a basis for the design of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF PREFERRED EMBODIMENTS OF THE INVENTION

A preferred embodiment of the present invention provides a method of determining the type of fuel used by the engine of a vehicle based on measurements of speciated hydrocarbon and nitrogen-oxygen compund ($NO_x$) emissions detected in the exhaust stream of the vehicle. The method receives information from an emissions sensor that measures such speciated hydrocarbon and $NO_x$ emissions. The sensor may be an open path sensor, such as a remote sensor that detects hydrocarbon emissions using methods such as ultraviolet and/or infrared light transmission, reflection, and detection; sound wave transmission, reflection, and detection; or any other method. In the alternative, the emissions sensor may be a closed path emissions sensor that is directly connected to the exhaust pipe of a vehicle to measure exhaust through one of the methods described above for open path emissions, or through a direct analytical method.

Figure 1:
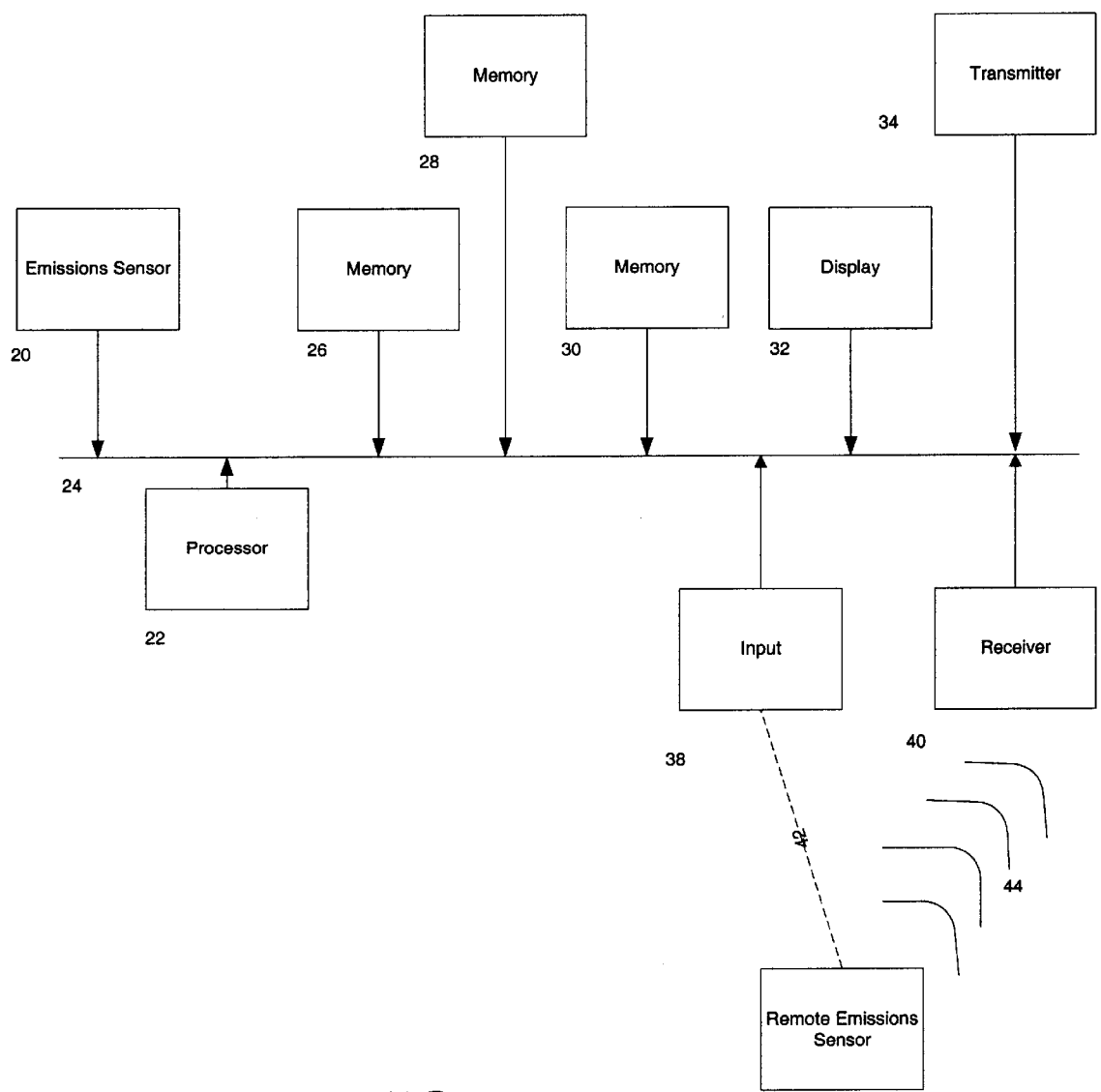
FIG. 1 is a block diagram illustrating several hardware components of preferred embodiments of the present invention.

FIG. 1 illustrates several elements of a preferred embodiment of the present invention. Referring to FIG. 1, an emissions sensor 20 delivers emissions-related data to a processor 22. In the embodiment illustrated in FIG. 1, the emissions sensor is part of the unit that contains the processor and the delivery is performed by a direct link such as a serial bus 24. However, the processor and emissions sensor may be separate, such as with the remote emissions sensor 36 illustrated in FIG. 1. Where a remote emissions sensor is used, the emissions data may be delivered to the processor 22 by a communications link 42 that delivers the data to an input port 38 such as a communications port. An optional wireless communications link 44 and receiver for such a wireless communication 46 are also illustrated in FIG. 1. The communications link 42 may be a direct wire, a wireless communications link, a global communications network such as the internet, or any other communications medium. In fact, although the present invention preferably uses data collected by an emissions sensor, it is not necessary to have an emissions sensor to practice the present invention, so long as emissions-related data is used.

Returning to FIG. 1, the system also includes a memory 26 which may be a memory such as a hard drive, random access memory and/or read only memory. Other memory devices 28 and 30 such as a CD-ROM, CD-R, DVD, floppy drive, ZIP drive, microdrive, compact flash, or other memory device may also be included. The device also optionally and preferably includes a display 32 and/or a transmitter 34 for providing output to a user or another device.

Figure 2:
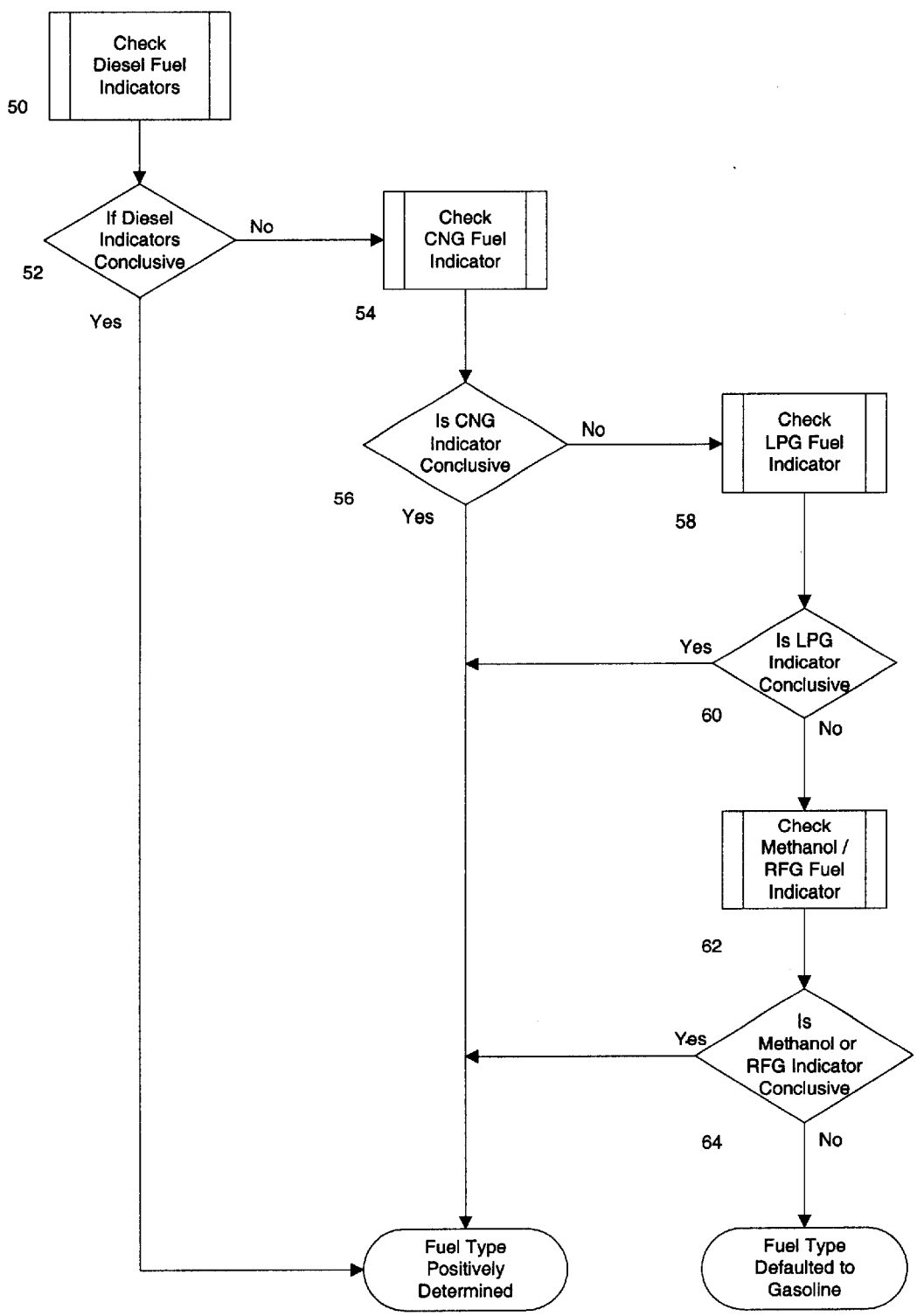
FIG. 2 is a flow chart illustrating the steps of a preferred embodiment of the selective elimination method of the present invention.

There are at least five major types of fuels used to power motor vehicles. These major types include gasoline and reformulated variations of gasoline, diesel fuel, compressed natural gas (CNG), liquified petroleum gas (LPG), and methanol. FIG. 2 illustrates a first preferred embodiment of the present inventive method of detecting fuel type based on these types of fuels. In accordance with this method, referred to herein as selective elimination, the method progressively compares the emissions data to anticipated indicators for individual fuel types. Preferably, the method starts with a fuel type that is easier to detect, such as diesel fuel as illustrated in FIG. 2, and proceeds to fuel types that are more difficult to detect, such as methanol as also illustrated in FIG. 2. In addition, other and/or additional fuel types may be checked, and the fuel types listed in FIG. 2 are only intended to be exemplary, although they are preferred. However, it is not necessary that the ordering of the selective elimination method followed this order or exactly corresponds to the order illustrated in FIG. 2. In accordance with this method, the fuel type checks abort when there is a positive identification of a particular fuel. This methodology lends itself well to faster processing because not all of the fuel types need to be checked.

Referring to FIG. 2, the method includes first checking the speciated hydrocarbon and $NO_x$ emissions measured by the emissions sensor against certain diesel fuel indicators (step 50). (A more detailed description of the methods of checking speciated emission measurements versus fuel type indicators will be presented below in the discussion relating to FIGS. 4-7.) If the check against the diesel fuel indicators yields a positive result (step 52), the system concludes that the fuel type has been positively determined (step 66). Optionally and preferably, the fuel type is then reported, whether on a display or through a transmitter or through some other communications means. Additionally, the fuel type may be stored in a memory in addition with other data related to the vehicle. Optionally, the emissions data record stored in memory can be flagged to indicate that the tested vehicle is diesel-fueled. If the method does not conclusively determine that the fuel type was diesel fuel, system may check a next indicator, such as those for CNG (step 54) to determine whether the measured hydrocarbons corresponds to the indicators for compressed natural gas (step 56). This procedure repeats for additional fuel types, such as LPG (step 58), and/or methanol and reformulated gasoline (RFG) (step 62). If none of the fuel type checks conclusively identifies a fuel type (step 4), the system optionally and preferably defaults to an assumption that the fuel type is gasoline or some other default fuel (step 68).

Figure 3:
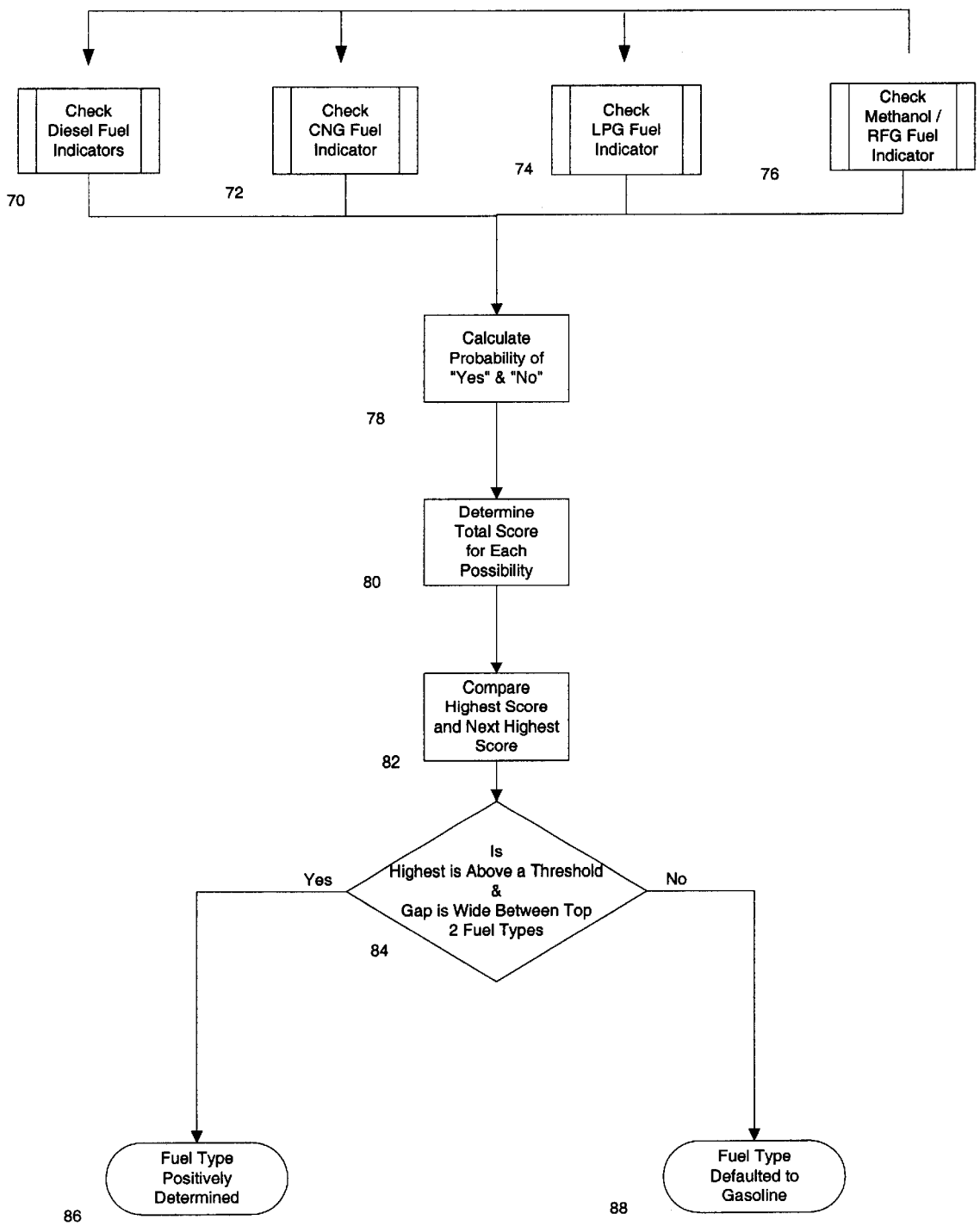
FIG. 3 is a block diagram of steps that may be followed in accordance with a preferred embodiment of the statistical election method of the present invention.

An alternate embodiment of the present invention, referred to herein as statistical election, may be used to preferably achieve an improved potential for precision and accuracy of fuel type determination. The preferred elements of the statistical election method are illustrated in FIG. 3. Referring to FIG. 3, a plurality of fuel type checks are performed by comparing hydrocarbon and nitrogen-oxygen ($NO_x$) compound emissions detected in a vehicle exhaust against the indicators for a plurality of fuel types. FIG. 3 illustrates the check being performed for diesel fuel (step 70), CNG (step 72), LPG (step 74) and methanol/RFG (step 76). However, it is not necessary that each of these fuel types be checked, and additional fuel types may also be check in accordance with the present invention.

After each fuel type is checked, the results of each check are scored based on the probability that the vehicle emissions match each of the fuel types (step 78). A higher probability would result from a determination that hydrocarbons and $NO_x$ found in the emissions are closer to, or preferably exceed, threshold indicators for a particular fuel type. The system scores each fuel type (step 80) by identifying the fuel type corresponding to the highest probability. These scores are then compared, and in particular the highest score is compared with the next highest score (step 82), because the wider the gap between the fuel type with the highest score and the next highest, the more confident that the determination will be. Although the system may optionally simply report that the fuel type having the highest score is the actual fuel type of the vehicle, preferably the method first determines whether the highest score is above a threshold score and that there is a large gap between the top two fuel type scores (step 84) before reporting a positive fuel type determination (step 86). If the highest score is not above a threshold or the gap between the two highest scores is very narrow, the system may report a default fuel type such as gasoline (step 88).

The results of the statistical election method address the certainty of the absence as well as the presence of fuel type indicators. For instance, diesel-fueled vehicles have a particular hydrocarbon signature. This signature includes (as compared to gasoline) a greater amount of methane, a higher concentration of carbonyl compounds, coupled with distinct $NO_x$ relationships. If there is a significant amount of nitrogen dioxide ($NO_2$) relative to total $NO_x$ in the exhaust, then it is also not likely that any other type of fuel being tested would create the exhaust signature that is being measured. An elevated measurement of $NO_2$, significant concentrations of carbonyl compounds, and elevated methane in the exhaust sample all contribute to a high statistical likelihood that the fuel type for the measured exhaust is diesel. However, elevated methane also occurs for CNG, so the methane test by itself does not contribute as much to the total score. Additionally, a lack of $NO_2$ almost certainly means that the fuel type cannot be diesel.

Figure 4:
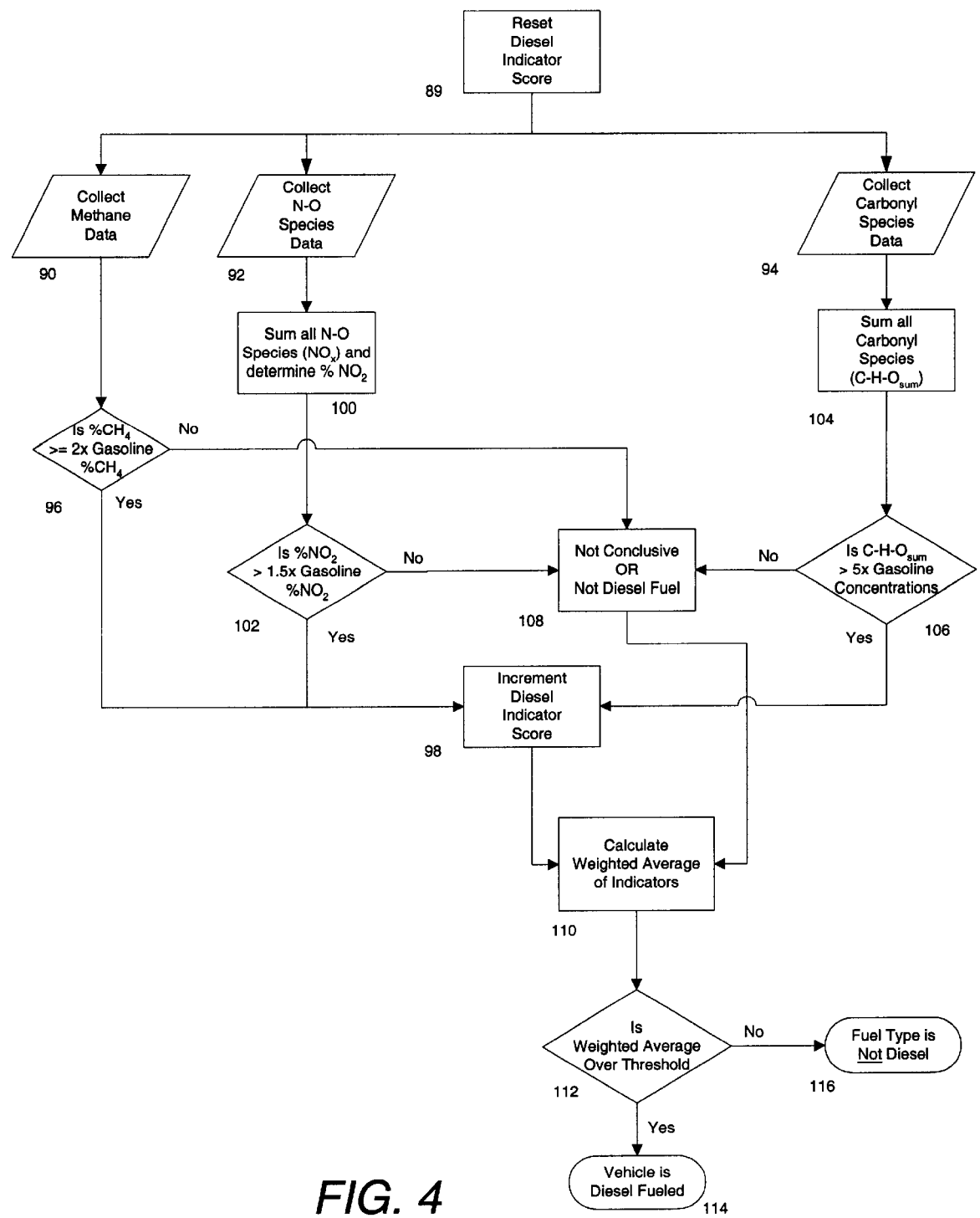
FIG. 4 is a flowchart illustrating the steps that may be used to determine the likelihood that vehicle emissions are indicative of diesel fuel.

FIG. 4 illustrates the steps that are followed to check hydrocarbon emissions measured in a vehicle exhaust against diesel fuel indicators. The data collected for this determination preferably includes but is not limited to methane, nitrogen-oxygen species (such as NO and $NO_2$), and carbonyl compounds such as those listed in the following table.

| COMPOUND | TYPE | WAVELENGTH (nm) |
| --- | --- | --- |
| Formaldehyde | Aldehyde | 325 |
| Acetaldehyde | Aldehyde | 285 |
| Acetone | Ketone | 278.0 |
| Propionaldehyde | Aldehyde | 293.0 |
| 2-Butanone | Aldehyde | 278.0 |
| Benzaldehyde | Aromatic Aldehyde | 284.1 |
| 2-Pentanenone | Carbonyl | 284.0 |
| o-Tolualdehyde | Aromatic Aldehyde | 292.2 |
| m-Tolueldehyde | Aromatic Aldehyde | 292.4 |
| p-Tolualdehyde | Aromatic Aldehyde | 285.5 |
| Phenol | Aromatic Alcohol | 275.1 |
| NO |  | 226 |
| $NO_2$ |  | 435 |

Carbonyl compounds comprise about 5% of the total hydrocarbons in gasoline exhaust. However, the percentage of carbonyl compounds in diesel exhaust is about four times higher than gasoline emissions. Diesel exhaust also contains a higher percentage of aromatic carbonyl compounds and unsaturated carbonyl compounds than gasoline exhaust. Formaldehyde, acetaldehyde and acetone exist in high concentrations from both diesel and gasoline exhausts.

In general, the top ten gasoline exhaust carbonyl compounds are formaldehyde, acetaldehyde, acetone, heptanal, crotonaldehyde, 2-butanone, propanal, acrolein, methacrolein, and benzaldehyde. The top ten diesel exhaust carbonyl compounds are formaldehyde, acetaldehyde, acetone, crotonaldehyde, m-tolualdehyde, 2-pentanone, benzaldehyde, 2,5-dimethylbenzaldehyde and 2-butanone. Formaldehyde, acetaldehyde and acetone account for about 76% of carbonyl emissions in gasoline but only about 50% of carbonyl emissions in diesel.

FIG. 4 illustrates a method of checking whether a fuel type is diesel fuel in accordance with the present invention. The method begins by resetting a diesel indicator score to zero or a predetermined baseline level (step 89). The system considers methane data (step 90) nitrogen oxide species data (step 92) and carbonyl species data (step 94). For the methane data, if the percentage of methane contained in the vehicle exhaust stream is greater than or equal to a threshold that is preferably twice that expected for gasoline (step 96), an increment is added to the diesel indicator score. If the methane level exceeds twice that which is expected for gasoline, the system increments the diesel indicator score (step 98) to reflect a higher likelihood that the fuel is diesel fuel.

The system also calculates total $NO_x$ (step 100) and determines whether the percentage of $NO_2$ exceeds a threshold that is preferably 1.5 times that which is typical for gasoline emissions (step 102). If the percentage of $NO_2$ relative to total $NO_x$ exceeds the threshold, the diesel indicator score is also incremented (step 98).

Similarly, all carbonyl species are summed (step 104), and the system checks whether the total carbonyl concentrations exceed a threshold that is preferably five times that which is typical for gasoline fueled vehicles (step 106), and if so the diesel indicator score is then incremented (step 98). Once all of the comparisons are done, a weighted average is calculated (step 110), and the system determines whether the weighted average exceeds a threshold level (step 112). If the weighted average exceeds the threshold, the system assumes that the vehicle is using diesel fuel (step 114). If the weighted average does not exceed the threshold, the system assumes that the fuel type is not diesel (step 116). In the embodiment that comprises statistical election, a probability may also be calculated based on the weighted average of the indicators and the threshold or based on other factors.

Figure 5:
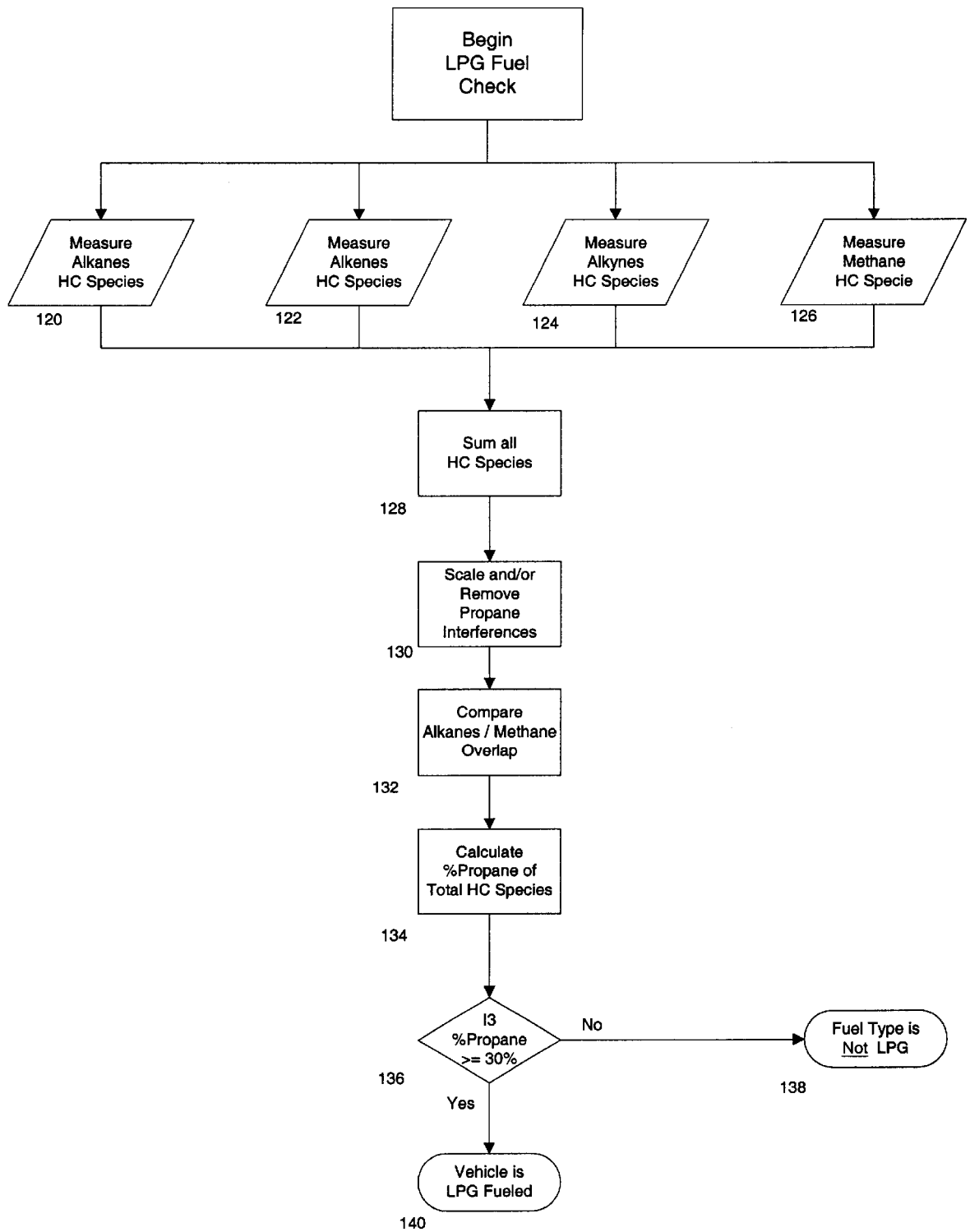
FIG. 5 is a flowchart illustrating the steps that may be used to determine the likelihood that vehicle emissions are indicative of liquefied petroleum gas.

FIG. 5 illustrates a preferred embodiment of the process of checking for whether vehicle emissions are indicative of LPG. LPG, a by-product of natural gas and petroleum refining, is a blend of propane and n-butane. United States regulations currently require propane to be the primary ingredient of automotive LPG, but in other parts of the world many blends of propane and n-butane are currently used. Regular or reformulated gasoline exhaust contains about 1% propane while LPG exhaust has propane concentrations of 30% or higher, depending upon the fuel blend used. The n-butane values are also somewhat higher than the concentrations found in regular or reformulated gasoline. As a result of propane concentrations being much higher for LPG than other fuel types, propane is an indicator emission in exhaust.

The difficulty is that propane has several absorption peaks that appear in more than one detector channel in a multi-channel hydrocarbon (HC) sensing system. Therefore, additional steps must be taken to remove the propane from other potential HC species. One embodiment of a method using discrete broadband HC detectors is to essentially superposition the propane response on each detector by removing the signal from as many other HC species that absorb in spectra for the given detector. This leaves only a propane response from the broadband detector.

For instance, propane belongs to the alkanes series of HC. If a second alkanes series channel exists in the system, such as methane, the signal on the detector contributed by other alkanes can be removed or scaled for each channel based upon an analysis of the detector's theoretical response to the HC species other than propane. Once all of the scaling is done, the remaining signal should be propane. Then compare the theoretical response from propane on the two detectors given the optical bandpass for each detector. From this comparison, a reasonable estimate can be made of propane found in the exhaust. The final step for LPG determination is to compare the calculated propane response of the system to the total amount of HC in the exhaust. If the propane is 30% or more of the total HC measurement, then there is a strong probability that the fuel is LPG.

Another embodiment of an LPG detection method is to use a spectrometer sensitive to the infrared region that has sufficient resolution to allow for a more direct measurement of propane. In this embodiment, assuming that the spectrometer has a fast enough response time, all detected HC species can be summed, then compared against the amount of propane measured. If the propane is 30% or more of the aggregate HC, then the vehicle is most likely fueled with LPG.

As noted above, FIG. 5 illustrates the above-described procedure in block diagram format. Data relating to species of alkanes, alkenes, alkynes, and methane are collected (steps 120, 122, 124, and 126), and the concentrations associated with each of such hydrocarbon species are summed (step 128). In accordance with the first embodiment described above, the system may then scale and/or remove interferences associated with propane (step 130) and then compare the overlap of alkanes and methane. In the alternative, steps 130 and 132 may be skipped if the system is equipped to receive a more direct measurement of propane. In either embodiment, whether propane is calculated based on total hydrocarbon species determinations or by direct measurement, the percentage of propane as a total of the hydrocarbon species is calculated (step 134). If the percentage of propane is 30% or more of the total hydrocarbon method (step 136), the system determines that there is a strong likelihood that the vehicle is LPG fueled (step 140). If the percentage of propane is less than 30%, the system presumes that the fuel type is not LPG (step 138).

Figure 6:
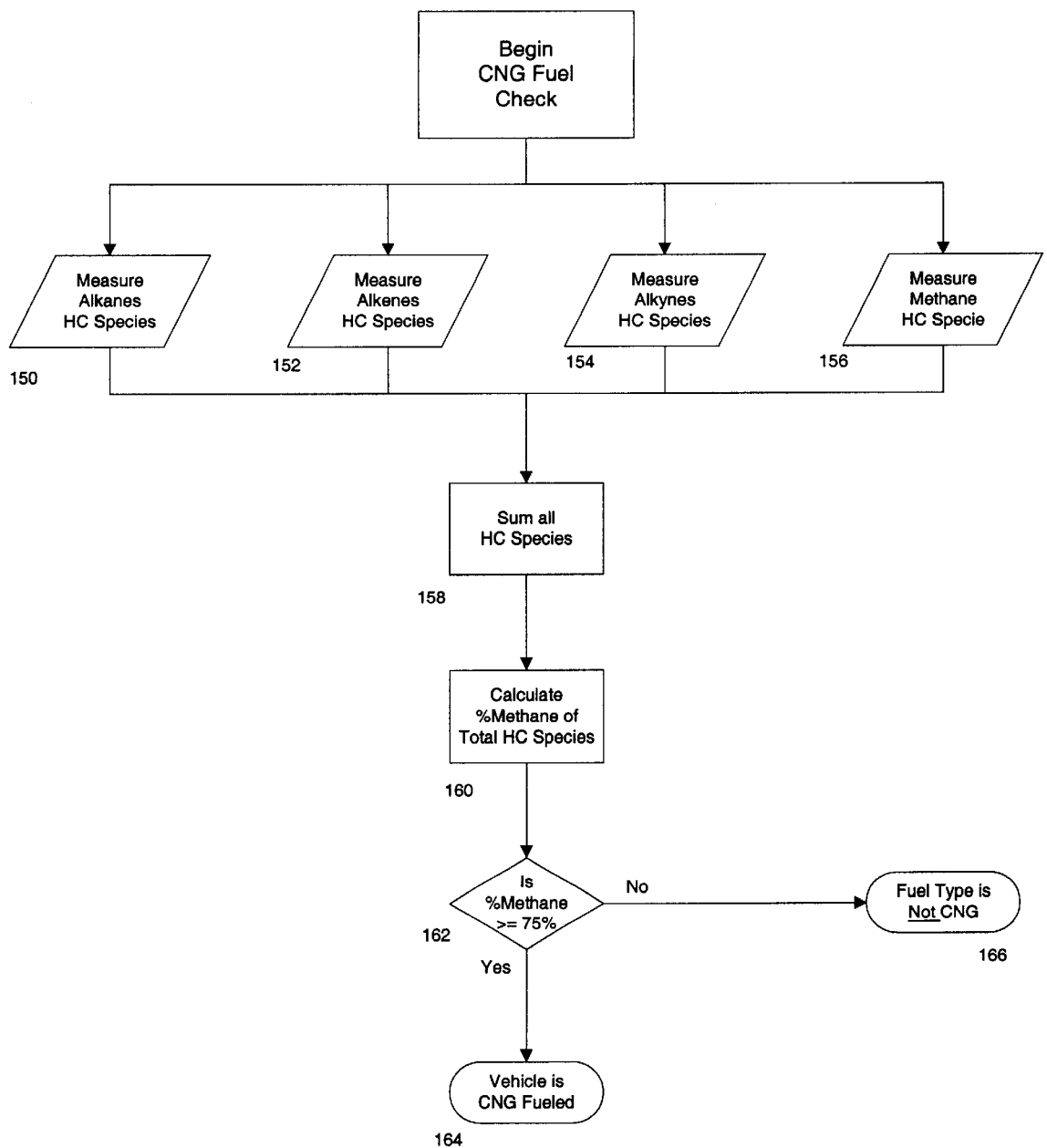
FIG. 6 is a flowchart illustrating the steps that may be used to determine the likelihood that vehicle emissions are indicative of compressed natural gas.

A preferred embodiment of the present inventive method of checking whether the fuel type is CNG is illustrated in FIG. 6. The main component of CNG fuel is methane. Thus, methane can be found in very high concentrations in CNG exhaust. Studies have found methane exhaust concentrations in the range of 75–88%. For this reason, a CNG-fueled vehicle will have an overwhelming amount of signal on the methane detector relative to all other hydrocarbon channels.

Like the method of checking whether a fuel type is LPG, FIG. 6 illustrates that the method also includes collecting data relating to alkanes, alkenes, alkynes, and methane in emissions (steps 150, 152, 154, and 156) for the CNG fuel type determination process. Using such information, the system sums all of the species (step 158) and calculates the percentage of methane existing in the sum of all the hydrocarbon species (step 160). The system then checks to see whether the percentage of methane equals or exceeds 75% (step 162). If the percentage of methane equals or exceeds 75%, the system determines that there is a strong likelihood that the vehicle is CNG fueled (step 164). If the percentage of methane is less than 75% of all hydrocarbon species, the system presumes that the fuel type is not CNG (step 166).

Methane burns at a lower temperature than gasoline, causing CNG exhaust to have a lower temperature than gasoline exhaust. As a result, catalytic converters designed for gasoline are less efficient at oxidizing pollutants in CNG exhaust. The LPG flame is hotter and consequently catalytic converters are more efficient at oxidizing LPG exhaust than CNG exhaust.

Figure 7:
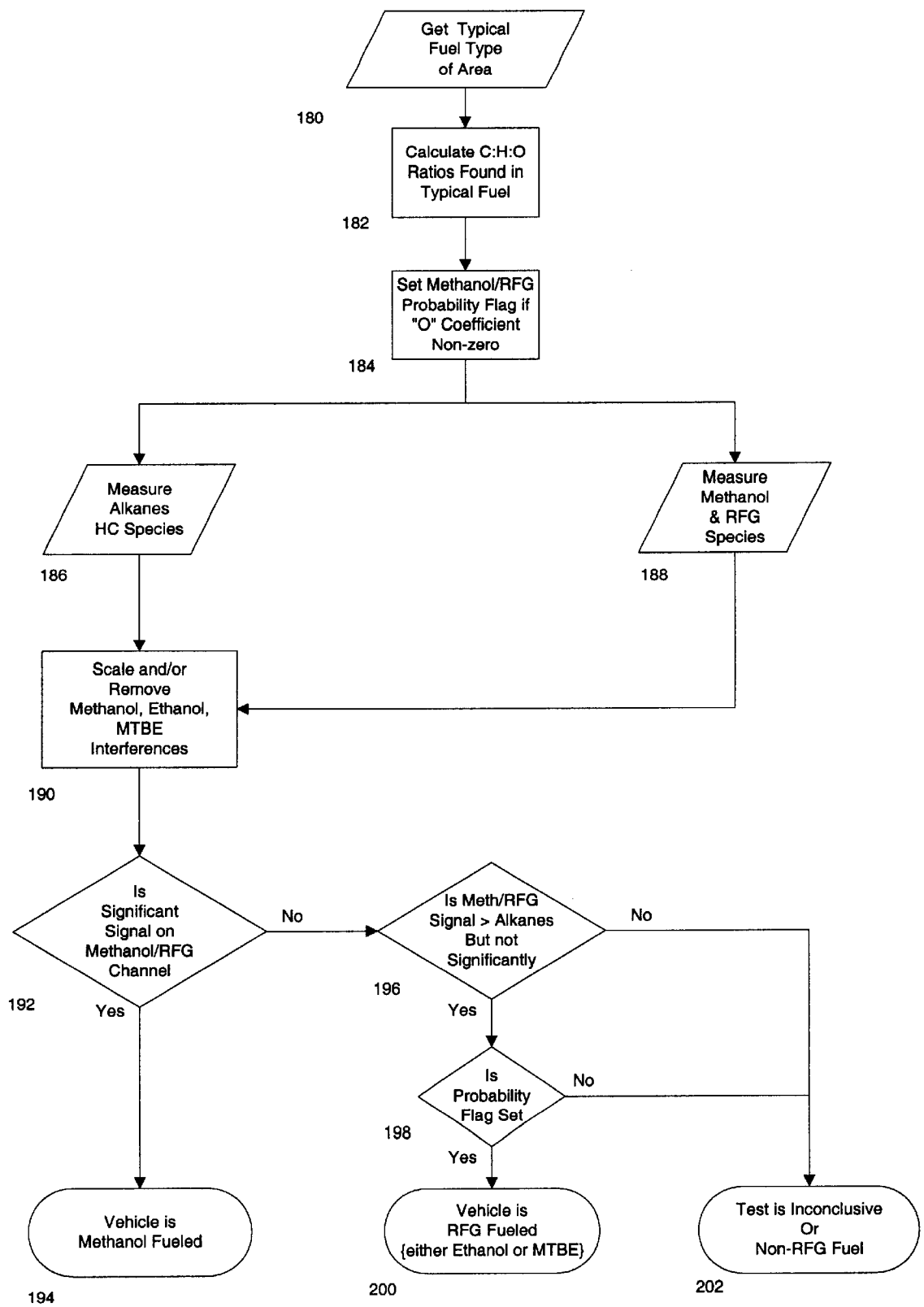
FIG. 7 is a flowchart illustrating the steps that may be used to determine the likelihood that vehicle emissions are indicative of methanol or reformulated gasoline.

FIG. 7 illustrates the steps that may be followed to determine whether a fuel type is methanol or reformulated gasoline (RFG). In carbon monoxide and ozone nonattainment areas, the Clean Air Act Amendments of 1990 require the use of gasoline additives that contain oxygen, such as ethanol or methyl tertiary butyl ether (MTBE). Gasoline containing oxygen additives are designed to help automobile engines to burn fuel with more complete combustion, thereby reducing emissions of volatile organic compounds (VOCs) and carbon monoxide.

The Oxygenated Fuels Provision of 1992 details gasoline specifications for 39 metropolitan areas that do not meet carbon monoxide air quality standards. Oxygenated gasoline sold in carbon monoxide nonattainment areas must contain 2.7% oxygen by weight and is required to be sold only during the winter months. The Reformulated Gasoline Provision of 1995 gives specifications for metropolitan areas that are in severe or extreme ozone nonattainment. RFG must contain 2.0% oxygen by weight and unlike the oxygenated gasoline must be sold all year round. RFG is also required to have a higher Reid vapor pressure and lower concentrations of benzene. It is most likely in these nonattainment areas where vehicle emissions testing will take place. Therefore, it is highly likely that vehicles sampled for their emissions will be fueled with RFG.

French researchers have discovered that methanol is a combustion product of oxygenated compounds as well as n-hexane and isooctane. Methanol therefore can be an interference with the determination of RFG. However, ethanol and MTBE were found in exhaust only when it was added to the original fuel. Given the potential for interferences with each other for the determination of these fuel types, it is best to check for each fuel type within the same algorithm.

M0 is a base gasoline with no methanol added, M15 is 15% methanol, M50 is 50% methanol, M85 is 85% methanol and M100 is pure methanol. Large quantities of methanol seem to be present in the exhaust of methanol fuel, particularly when the original fuel contains a high concentration of methanol. The methanol fuel type determination will be most effective in areas where automotive fuels are mostly alcohol.

Methanol is highly corrosive and requires special fuel plumbing of materials that are not affected by the corrosiveness. This makes methanol a less likely fuel type when many types of fuels are available in a given region. This fact assists also in the determination of methanol in areas such as the United States where it is currently not very likely that methanol will be a fuel of choice.

For effective determination of either of these fuel types mentioned in this segment of the disclosure, it is useful to have a file for a system to have advanced knowledge of the predominant fuel type in the region where emissions testing is taking place. The fuel type needs to be expressed to the system in terms of the Carbon:Hydrogen:Oxygen (C:H:O) mix within the fuel. The following short table is an example of the C:H:O mix of typical fuels:

| Fuel | Wt Fraction C | Wt Fraction H | Wt Fraction O | Formula |
| --- | --- | --- | --- | --- |
| Diesel | 0.86 | 0.14 | 0 | $CH_{1.95}O_0$ |
| Regular gas | 0.87 | 0.13 | 0 | $CH_{1.78}O_0$ |
| Reformulated | 0.85 | 0.13 | 0.02 | $CH_{1.84}O_{.018}$ |

An oxygenated fuel such as RFG will have an oxygen weight fraction that is non-zero. This helps the system determine if it is even possible for an oxy-fueled vehicle to be tested. Once this is determined, then measurement of the alkanes series of HC and a measurement of a discrete methanol/RFG HC are taken.

After removing potential overlaps of other HC species from the two mentioned HC channels, a comparison is made on how significant the signal from the methanol/RFG channel is relative to the signal on the alkanes channel. A methanol-fueled vehicle will have a greater proportion of the aggregate of the two HC channels in proportion to the mix of methanol that exists in the fuel. However, a non-methanol fueled vehicle will have virtually the same signal on the alkanes as the methanol/RFG specific channel. An RFG-fueled vehicle will have a slightly greater signal on the methanol/RFG channel than the broader alkanes series channel. Combining the fact that it is predetermined in a setup file within the fuel type determination system that there is the possibility of RFG with the actual emissions measurements gives a reasonable statistical likelihood that RFG is the fuel type for the tested vehicle.

As noted above, these steps are illustrated in FIG. 7. Referring to FIG. 7, the steps that may be followed to determine whether a fuel type is methanol or RFG include obtaining information relating to a fuel type expected to be found in the particular area (step 180) and calculating the C:H:O mix that would be expected to be found in the typical fuel (step 182). A methanol/RFG probability flag is set if the oxygen coefficient in the C:H:O: ratio is anything other than zero (step 184). The alkanes species and methanol/RFG species are measured (steps 186 and 188) and methanol, ethanol, and MTBE interferences are removed (step 190). If the signal on the methanol/RFG channel is determined to be significantly greater than that on the alkanes channel (step 192), the method assumes that the vehicle is fueled by methanol (step 184). If the methanol/RFG signal is greater than the alkanes signal, but not significantly so (step 196), and the probability flag has been set (step 198), then the method assumes that the vehicle is fueled by an RFG such as ethanol or MTBE (step 200). If the methanol/RFG signal is not greater than the alkanes signal, or if the probability flag is not set, the method determines that the test is inconclusive or non-RFG/methane fuel (step 202).

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, all of which may fall within the scope of the invention.

What is claimed is:

1. A method of determining the type of fuel used by a vehicle, comprising:
   receiving first data collected by an emissions sensor, wherein the first data corresponds to a plurality of measured hydrocarbon concentrations in a vehicle exhaust stream;
   receiving second data collected by the emissions sensor, wherein the second data corresponds to measured nitrogen-oxygen compound concentrations in the vehicle exhaust stream;
   identifying at least one hydrocarbon threshold level corresponding to a first fuel type;
   comparing the first data to at least one of the hydrocarbon threshold levels; and
   determining whether the measured hydrocarbon concentrations correspond to at least one of the hydrocarbon threshold levels;
   identifying at least one nitrogen-oxygen compound threshold level corresponding to the first fuel type;
   comparing the second data to at least one of the nitrogen-oxygen compound threshold levels; and
   determining whether the measured nitrogen-oxygen compound concentrations correspond to at least one of the nitrogen-oxygen compound threshold levels.

2. The method of claim 1 wherein the first determining step determines that the measured hydrocarbon concentrations do not correspond to at least one of the hydrocarbon threshold levels, and the method comprises the additional steps of:
   identifying at least one hydrocarbon threshold level corresponding to a second fuel type;
   comparing the data to at least one of the hydrocarbon threshold levels corresponding to the second fuel type; and
   determining whether the measured hydrocarbon concentrations correspond to at least one of the hydrocarbon threshold levels corresponding to the second fuel type.

3. The method of claim 1 wherein the second determining step determines that the measured nitrogen-oxygen compound concentrations do not correspond to at least one of the nitrogen-oxygen compound threshold levels, and the method comprises the additional steps of:
   identifying at least one nitrogen-oxygen compound threshold level corresponding to a second fuel type;
   comparing the second data to at least one of the nitrogen-oxygen compound threshold levels corresponding to the second fuel type; and
   determining whether the measured nitrogen-oxygen compound concentrations correspond to at least one of the nitrogen-oxygen compound threshold levels corresponding to the second fuel type.

4. The method of claim 1 wherein the first fuel type is selected from the group comprising diesel fuel, gasoline, compressed natural gas, methanol, reformulated gasoline, and liquified petroleum gas.

5. The method of claim 1 wherein each identifying step comprises retrieving the at least one threshold level corresponding to a first fuel type from a computer memory.

6. The method of claim 1 wherein at least one of the threshold levels comprises a percentage, and correspondence in at least one of the determining steps comprises a determination that the measured concentration is equal to or greater than the percentage.

7. The method of claim 1 wherein at least one of the threshold levels comprises a range, and correspondence in the at least one of the determining steps comprises a determination that the measured concentration falls within the range.

8. The method of claim 1 wherein the first fuel type comprises diesel fuel, and the first comparing step comprises comparing measured concentrations to threshold levels of methane and carbonyl species and the second comparing step comprises comparing measured concentrations to threshold concentrations of nitrogen dioxide.

9. The method of claim 1 wherein the first fuel type comprises compressed natural gas, and the first comparing step comprises:
   summing measured concentrations of alkanes, alkenes, alkynes, and methane; and
   comparing the measured concentration of methane to the total sum of alkanes, alkenes, alkynes, and methane.

10. The method of claim 1 wherein the first fuel type comprises liquified petroleum gas, and the first comparing step comprises:
    determining a total hydrocarbon measurement comprising a sum of measured concentrations of alkanes, alkenes, alkynes, and methane;
    determining a percentage of propane relative to the total hydrocarbon measurement; and
    determining whether the percentage of propane exceeds a predetermined propane threshold.

11. The method of claim 1 comprising the additional steps of:
    identifying relative concentrations of carbon, hydrogen, and oxygen that are typical for a reference fuel;
    determining whether the relative concentration of oxygen is greater than zero;
    selecting, from the plurality of measured hydrocarbon concentrations, a first concentration corresponding to alkanes and a second concentration corresponding to methanol and reformulated gasoline species;
    scaling the first concentration and the second concentration to adjust for at least one interference; and comparing the first concentration and the second concentration.

12. A method of determining the type of fuel used by a vehicle, comprising:
   receiving data collected by an emissions sensor, wherein the data corresponds to a plurality of measured hydrocarbon and nitrogen-oxygen compound concentrations in a vehicle exhaust stream;
   calculating, for each of a plurality of possible fuel types, an associated probability, the associated probability corresponding to the plurality of measured hydrocarbon and nitrogen-oxygen compound concentrations;
   selecting, from the associated probabilities calculated in the calculating step, a highest probability; and
   reporting the possible fuel type having the associated probability that is the highest probability.

13. The method of claim 12 wherein:
   one of the possible fuel types comprises diesel fuel;
   the first calculating step, when performed for diesel fuel, comprises comparing measured concentrations to threshold levels of methane and carbonyl species; and
   the second calculating step, when performed for diesel fuel, comprises comparing measured concentrations to threshold concentrations of nitrogen dioxide.

14. The method of claim 12 wherein one of the possible fuel types comprises compressed natural gas, and the first calculating step, when performed for compressed natural gas, comprises:
   determining a total hydrocarbon measurement comprising a sum of measured concentrations of alkanes, alkenes, alkynes, and methane;
   determining a percentage of methane in the total hydrocarbon measurement; and
   determining whether the percentage of methane exceeds a predetermined methane threshold.

15. The method of claim 12 wherein one of the possible fuel types comprises liquified propane gas, and the calculating step, when performed for liquified petroluem gas, comprises:
   determining a total hydrocarbon measurement comprising a sum of measured concentrations of alkanes, alkenes, alkynes, and methane;
   determining a percentage of propane in the total hydrocarbon measurement; and
   determining whether the percentage of propane exceeds a predetermined propane threshold.

16. The method of claim 12 wherein the possible fuel types comprise at least one of methanol and reformulated gasoline, and wherein the first calculating step, when performed for methanol or reformulated gasoline, comprises:
   identifying relative concentrations of carbon, hydrogen, and oxygen that are typical for a reference fuel;
   determining whether the relative concentration of oxygen is greater than zero;
   selecting, from the plurality of measured hydrocarbon concentrations, a first concentration corresponding to alkanes and a second concentration corresponding to methanol and reformulated gasoline species;
   scaling the first concentration and the second concentration to adjust for at least one interference; and
   comparing the first concentration and the second concentration.

17. A system for determining the type of fuel used by a vehicle, comprising of:
   an open path emissions sensor capable of measuring a plurality of measured hydrocarbon and nitrogen-oxygen compound concentrations in a vehicle exhaust stream;
   a processor in communication with the emissions sensor; and
   a memory in communication with the processor;
   wherein the memory contains computer program instructions that are capable of instructing the processor to:
      retrieve, from a database, at least one hydrocarbon threshold level corresponding to a first fuel type;
      compare the measured hydrocarbon concentrations to at least one of the hydrocarbon threshold levels; and
      determine whether the measured hydrocarbon concentrations correspond to the at least one hydrocarbon threshold level;
      retrieve, from a database, at least one nitrogen-oxygen compound threshold level corresponding to the first fuel type;
      compare the measured nitrogen-oxygen compound concentrations to at least one of the nitrogen-oxygen compound threshold levels; and
      determine whether the measured nitrogen-oxygen compound concentrations correspond to at least one of the nitrogen-oxygen compound threshold levels.

18. The system of claim 17, wherein the memory contains additional program instructions so that, if the processor determines that the measured hydrocarbon concentrations do not correspond to at least one of the hydrocarbon threshold levels, the processor may be further instructed to:
   identify at least one hydrocarbon threshold level corresponding to a second fuel type;
   compare the measured hydrocarbon concentrations to at least one of the hydrocarbon threshold levels corresponding to the second fuel type; and
   determine whether the measured hydrocarbon concentrations correspond to at least one of the hydrocarbon threshold levels corresponding to the second fuel type.

19. The system of claim 17, wherein the memory contains additional program instructions so that, if the processor determines that measured nitrogen-oxygen compound concentrations do not correspond to at least one of the nitrogen-oxygen compound threshold levels, the processor may be further instructed to:
   identify at least one nitrogen-oxygen compound threshold level corresponding to a second fuel type;
   compare the measured nitrogen-oxygen compound concentrations to at least one of the nitrogen-oxygen compound threshold levels corresponding to the second fuel type; and
   determine whether the measured nitrogen-oxygen compound concentrations correspond to at least one of the nitrogen-oxygen compound threshold levels corresponding to the second fuel type.

20. A system for determining the type of fuel used by a vehicle, comprising:
   an emissions sensor capable of measuring a plurality of measured hydrocarbon and nitrogen-oxygen compound concentrations in a vehicle exhaust stream;
   a processor in communication with the emissions sensor; and
   a carrier in communication with the processor;
   wherein the carrier contains computer program instructions that instruct the processor to:

calculate, for each of a plurality of possible fuel types, a first set of associated probabilities, the first set of associated probabilities corresponding to the plurality of measured hydrocarbon concentrations and the plurality of measured nitrogen-oxygen compound concentrations; and select, from the associated probabilities calculated by the processor, a highest probability.

21. A system for identifying the type of fuel used by a vehicle, comprising:

a means for detecting a plurality of measured hydrocarbon and nitrogen-oxygen compound concentrations in the emissions of a vehicle, a means for identifying at least one hydrocarbon threshold level corresponding to at least one fuel type;

a means for comparing the measured hydrocarbon concentrations to at least one of the hydrocarbon threshold levels to determine whether the measured hydrocarbon concentrations correspond to a corresponding fuel type;

a means for identifying at least one nitrogen-oxygen compound threshold level corresponding to at least one of the fuel types; and a means for comparing the measured nitrogen-oxygen compound concentrations to at least one of the nitrogen-oxygen compound threshold levels to determine whether the measured nitrogen-oxygen compound concentrations correspond to a corresponding fuel type.

* * * * *